US010034966B2

(12) United States Patent
Bettinger et al.

(10) Patent No.: US 10,034,966 B2
(45) Date of Patent: *Jul. 31, 2018

(54) COATED VASO-OCCLUSIVE DEVICE AND METHODS FOR TREATMENT OF ANEURYSMS (71) Applicant: Carnegie Mellon University, Pittsburgh, PA (US)

(72) Inventors: Christopher J. Bettinger, Pittsburgh, PA (US); Michael Bruce Horowitz, Jones Mills, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/599,634

(22) Filed: May 19, 2017

(65) Prior Publication Data
US 2018/0008748 A1 Jan. 11, 2018

Related U.S. Application Data (63) Continuation of application No. 14/775,078, filed as application No. PCT/US2014/024158 on Mar. 12, 2014, now Pat. No. 9,655,999.

(60) Provisional application No. 61/851,677, filed on Mar. 12, 2013.

(51) Int. Cl.
A61L 29/08 (2006.01)
A61L 31/16 (2006.01)
A61L 31/06 (2006.01)
A61L 31/10 (2006.01)
A61L 29/16 (2006.01)
A61M 25/00 (2006.01)
A61K 31/352 (2006.01)
A61L 29/14 (2006.01)
A61B 17/12 (2006.01)

(52) U.S. Cl.
CPC ........ A61L 29/085 (2013.01); A61B 17/1215 (2013.01); A61B 17/12031 (2013.01); A61B 17/12113 (2013.01); A61B 17/12145 (2013.01); A61K 31/352 (2013.01); A61L 29/148 (2013.01); A61L 29/16 (2013.01); A61L 31/06 (2013.01); A61L 31/10 (2013.01); A61L 31/16 (2013.01); A61M 25/0045 (2013.01); A61L 2300/252 (2013.01); A61L 2300/602 (2013.01); A61L 2300/604 (2013.01); A61L 2420/04 (2013.01); A61L 2420/08 (2013.01); A61L 2430/36 (2013.01)

(58) Field of Classification Search
None
See application file for complete search history.

(56) References Cited

U.S. PATENT DOCUMENTS

| 5,022,888 A | 6/1991 | Lindee |
| 5,162,826 A | 11/1992 | Morgan et al. |
| 5,262,083 A | 11/1993 | Mori et al. |
| 5,272,172 A | 12/1993 | Fujii et al. |
| 5,869,079 A | 2/1999 | Wong et al. |
| 6,608,040 B1 | 8/2003 | Lin et al. |
| 6,624,138 B1 | 9/2003 | Sung et al. |
| 6,998,418 B1 | 2/2006 | Sung et al. |
| 7,070,607 B2 | 7/2006 | Murayama et al. |
| 7,282,220 B1 | 10/2007 | Sung et al. |
| 7,306,624 B2 | 12/2007 | Yodfat et al. |
| 7,572,290 B2 | 8/2009 | Yodfat et al. |
| 7,649,014 B2 | 1/2010 | Zhang et al. |
| 7,896,899 B2 | 3/2011 | Patterson et al. |
| 7,942,925 B2 | 5/2011 | Yodfat et al. |
| 8,022,101 B2 | 9/2011 | Hedman |
| 8,093,288 B2 | 1/2012 | Zhang et al. |
| 8,119,599 B2 | 2/2012 | Redman et al. |
| 8,187,255 B2 | 5/2012 | Weber et al. |
| 8,198,248 B2 | 6/2012 | Hedman et al. |
| 8,211,938 B2 | 7/2012 | Hedman |
| 8,241,654 B2 | 8/2012 | Stopek |
| 8,273,100 B2 | 9/2012 | Martinez |
| 8,283,322 B2 | 10/2012 | Slusarewicz et al. |
| 8,288,129 B2 | 10/2012 | Lai et al. |
| 8,293,530 B2 | 10/2012 | Burgess et al. |
| 8,303,974 B2 | 11/2012 | Macdonald et al. |
| 8,388,643 B2 | 3/2013 | Murayama et al. |
| 8,388,677 B2 | 3/2013 | Herrmann |
| 2002/0040239 A1 | 4/2002 | Murayama et al. |
| 2003/0004568 A1 | 1/2003 | Ken et al. |
| 2003/0049301 A1 | 3/2003 | Hedman |
| 2003/0100945 A1 | 5/2003 | Yodfat et al. |

(Continued)

FOREIGN PATENT DOCUMENTS

| EP | 1156759 A1 | 11/2001 |
| EP | 1260237 A1 | 11/2002 |

(Continued)

OTHER PUBLICATIONS

Abizaid et al., "New Drug-Eluting Stents: An Overview on Biodegradable and Polymer-Free Next-Generation Stent Systems", Circ Cardiovascualr Interv., 2010, pp. 384-393, vol. 3.

(Continued)

Primary Examiner — Robert A Wax
Assistant Examiner — Quanglong N Truong
(74) Attorney, Agent, or Firm — The Webb Law Firm (57) ABSTRACT A method is described herein for the treatment of intracranial aneurysms. The method comprises inserting into an aneurysm an embolism coil coated with a polymeric coating comprising a genipin, such as genipin or a derivative thereof, thereby increasing the stability of clots within the aneurysm. According to one example, the coating is a poly(L-lactide-co-glycolide) (PLGA) is used to release genipin to crosslink fibrin clots thereby creating more stable occlusions. Increased clotting can improve segregation of the weakened portion of the blood vessel from the rest of the vasculature and reduce the risk of recurrence.

20 Claims, 4 Drawing Sheets

(56) References Cited

U.S. PATENT DOCUMENTS

| | | |
|---|---|---|
| 2004/0193246 A1 | 9/2004 | Ferrera |
| 2005/0149175 A1 | 7/2005 | Hunter et al. |
| 2005/0163818 A1 | 7/2005 | Sung et al. |
| 2005/0165467 A1 | 7/2005 | Hunter et al. |
| 2006/0099191 A1 | 5/2006 | Hoh et al. |
| 2007/0014831 A1 | 1/2007 | Sung et al. |
| 2007/0093889 A1 | 4/2007 | Wu et al. |
| 2007/0128246 A1 | 6/2007 | Hossainy et al. |
| 2007/0141009 A1 | 6/2007 | Buiser et al. |
| 2007/0150045 A1 | 6/2007 | Ferrera |
| 2007/0202143 A1 | 8/2007 | Hedman |
| 2007/0299518 A1 | 12/2007 | Ruane |
| 2008/0029390 A1 | 2/2008 | Roche et al. |
| 2008/0069858 A1 | 3/2008 | Weber |
| 2009/0164013 A1 | 6/2009 | Cruise et al. |
| 2009/0186229 A1 | 7/2009 | Muller et al. |
| 2009/0258050 A1 | 10/2009 | Lindsay et al. |
| 2009/0311300 A1 | 12/2009 | Wittchow |
| 2010/0080838 A1 | 4/2010 | Stopek |
| 2010/0087854 A1 | 4/2010 | Stopek et al. |
| 2010/0183699 A1 | 7/2010 | Wan et al. |
| 2010/0198334 A1 | 8/2010 | Yodfat et al. |
| 2010/0274276 A1 | 10/2010 | Chow et al. |
| 2011/0086234 A1 | 4/2011 | Stasko et al. |
| 2011/0118777 A1 | 5/2011 | Patterson et al. |
| 2012/0189584 A1 | 7/2012 | Schek et al. |
| 2012/0294823 A1 | 11/2012 | Aramwit |
| 2012/0310271 A1 | 12/2012 | Kwon |
| 2012/0323211 A1 | 12/2012 | Ogle et al. |

FOREIGN PATENT DOCUMENTS

| | | |
|---|---|---|
| EP | 0941130 B1 | 3/2003 |
| EP | 1432312 A1 | 6/2004 |
| EP | 1545505 A2 | 6/2005 |
| EP | 1610666 A2 | 1/2006 |
| EP | 1976484 A2 | 10/2008 |
| EP | 2056748 A2 | 5/2009 |
| EP | 2168610 A2 | 3/2010 |
| EP | 2214747 A2 | 8/2010 |
| EP | 2266639 A1 | 12/2010 |
| EP | 1991111 B1 | 4/2011 |
| EP | 1359953 B1 | 5/2011 |
| EP | 2234798 B1 | 3/2012 |
| EP | 2425800 A2 | 3/2012 |
| EP | 2491868 A1 | 8/2012 |
| WO | 0044306 A1 | 8/2000 |
| WO | 02089863 A1 | 11/2002 |
| WO | 03020031 A1 | 3/2003 |
| WO | 2004012676 A2 | 2/2004 |
| WO | 2004091381 A2 | 10/2004 |
| WO | 2005113035 A2 | 12/2005 |
| WO | 2007092179 A2 | 8/2007 |
| WO | 2008027902 A2 | 3/2008 |
| WO | 2009067431 A2 | 5/2009 |
| WO | 2009105265 A2 | 8/2009 |

OTHER PUBLICATIONS

Almog et al., "Genipin—A Novel Fingerprint Reagent with Colorimetric and Fluorogenic Activity", J Forensic Sci, Mar. 2004, pp. 1-3, vol. 49, No. 2.

Avila et al., "Corneal crosslinking with genipin, comparison with UV-Riboflavin in ex-vivo model", Molecular Vision, 2012, pp. 1068-1073, vol. 18.

Bigi et al., "Stabilization of gelatin films by crosslinking with genipin", Biomaterials, 2002, pp. 4827-4832, vol. 23.

Butler et al., "Mechanism and Kinetics of the Crosslinking Reaction between Biopolymers Containing Primary Amine Groups and Genipin", Journal of Polymer Science: Part A: Polymer Chemistry, 2003, pp. 3941-3953, vol. 41.

Chang et al., "A genipin-crosslinked gelatin membrane as wound-dressing material: in vitro and in vivo studies", J. Biomater. Sci. Polymer Edn, 2003, pp. 481-495, vol. 14, No. 5.

Chang et al., "Acellular Bovine Pericardia with Distinct Porous Structures Fixed with Genipin as an Extracellular Matrix", Tissue Engineering, 2004, pp. 881-892, vol. 10.

Chen et al., "A novel pH-sensitive hydrogel composed of N,O-carboxymethyl chitosan and alginate cross-linked by genipin for protein drug delivery", Journal of Controlled Release, 2004, pp. 285-300, vol. 96.

Chen et al., "An in vivo evaluation of a biodegradable genipin-cross-linked gelatin peripheral nerve guide conduit material", Biomaterials, 2005, pp. 3911-3918, vol. 26.

Groden et al., "Histological Findings in Ruptured Aneurysms Treated with GDCs: Six Examples at Varying Times after Treatment", AJNR Am J Neuroradiol, Apr. 2003, pp. 579-584, vol. 24.

Lee et al., "Colorimetric determination of amino acids using genipin from Gardenia jasminoides", Analytica Chimica Acta, 2003, pp. 267-274, vol. 480.

Levinton-Shamuilov et al., "Genipin, a Novel Fingerprint Reagent With Colorimetric and Fluorogenic Activity, Part II: Optimization, Scope and Limitations", Journal of Forensic Sciences, Dec. 2005, pp. 1-5.

Liang et al., "Effects of crosslinking degree of an acellular biological tissue on its tissue regeneration pattern", Biomaterials, 2004, pp. 3541-3552, vol. 25.

Lima et al., "Genipin enhances the mechanical properties of tissue-engineered cartilage and protects against inflammatory degradation when used as a medium supplement", Journal of Biomedical Materials Research Part A, 2009, pp. 692-700.

Ma et al., "Drug-eluting Stent Coatings", Intery Cardiol., 2012, pp. 73-83, vol. 4, No. 1.

Murayama et al., "Ion Implantation and Protein Coating of Detachable Coils for Endovascular Treatment of Cerebral Aneurysms: Concepts and Preliminary Results in Swine Models", Neurosurgery, Jun. 1997, pp. 1233-1244, vol. 40, No. 6.

Piotin et al., "Intracranial Aneurysms Coiling with Matrix: Immediate Results in 152 Patients and Midterm Anatomic Follow-Up From 115 Patients", Stroke, 2009, pp. 321-323, vol. 40.

Pubchem. CID 442424, Jun. 24, 2006, pp. 1-17, [online], Retrieved from the Internet: https://pubchem.ncbi.nlm.nih.gov/compound/442424.

Reinges et al., "Bare, Bio-Active and Hydrogel-Coated Coils for Endovascular Treatment of Experimentally Induced Aneurysms: Long-Term Histological and Scanning Electron Microscopy Results", Interventional Neuroradiology, 2010, pp. 139-150, vol. 16.

Shastri, "Non-Degradable Biocompatible Polymers in Medicine: Past, Present and Future", Current Pharmaceutical Biotechnology, 2003, pp. 331-337, vol. 4.

Sundararaghavan et al., "Genipin-induced changes in collagen gels: Correlation of mechanical properties to fluorescence", Journal of Biomedical Materials Research Part A, 2008, pp. 308-320.

Sung et al., "Evaluation of gelatin hydrogel crosslinked with various crosslinking agents as bioadhesives: In vitro study", J. Biomed. Mater. Res., 1999, pp. 520-530.

Sung et al., "Gelatin-derived bioadhesives for closing skin wounds: an in vivo study", J. Biomater. Sci. Polymer Edn, 1999, pp. 751-771, vol. 10, No. 7.

Sung et al., "Stability of a biological tissue fixed with a naturally occurring crosslinking agent (genipin)", Journal of Biomedical Materials Research Part A, 2001, pp. 538-546.

Sung et al., "Crosslinking of biological tissues using genipin and/or carbodiimide", Journal of Biomedical Materials Research Part A, 2003, pp. 427-438.

Touyama et al., "Studies on the Blue Pigments Produced from Genipin and Methylamine. II. On the Formation Mechanisms of Brownish-Red Intermediates Leading to the Blue Pigment Formation", Chem. Pharm. Bull., 1994, pp. 1571-1578, vol. 42, No. 8.

Tsai et al., "Effects of heparin immobilization on the surface characteristics of a biological tissue fixed with a naturally occurring crosslinking agent (genipin): an in vitro study", Biomaterials, 2001, pp. 523-533, vol. 22.

(56) References Cited

OTHER PUBLICATIONS

Yan et al., "Genipin-cross-linked collagen/chitosan biomimetic scaffolds for articular cartilage tissue engineering applications", Journal of Biomedical Materials Research A, Nov. 2010, pp. 465-475, vol. 95A.

Yao et al., "Preparation of Networks of gelatin and genipin as degradable biomaterials", Materials Chemistry and Physics, 2004, pp. 204-208, vol. 83.

Yao et al., "Calvarial bone response to a tricalcium phosphate-genipin crosslinked gelatin composite", Biomaterials, 2005, pp. 3065-3074, vol. 26.

Wang et al., "Genipin inhibits endothelial exocytosis via nitric oxide in cultured human umbilical vein endothelial cells", Acta Pharmacol Sin, May 2009, pp. 589-596, vol. 30, No. 5.

COATED VASO-OCCLUSIVE DEVICE AND METHODS FOR TREATMENT OF ANEURYSMS

CROSS REFERENCE TO RELATED APPLICATIONS

This application is a continuation of U.S. patent application Ser. No. 14/775,078, filed Sep. 11, 2015, which was a national stage of International Patent Application No. PCT/US2014/024158, filed Mar. 12, 2014, which claims the benefit of U.S. Provisional Patent Application No. 61/851,677, Filed Mar. 12, 2013, each of which are incorporated herein by reference in its entirety.

BACKGROUND

Intracranial cerebral aneurysms are most commonly found as arterial saccular dilatations located at points where parent arteries bifurcate into branch vessels. The incidence of these lesions in human autopsy studies is approximately 5%. Most aneurysms remain asymptomatic due to a low rupture rate of 0.5 to 4% per year depending upon their size, shape, and location (average rate of rupture 1%). The mortality rate after rupture is between 30 and 60% if no treatment is administered. Of the remaining patients, outcome depends upon (1) the patient's neurologic condition when he/she presents for care and (2) the complexity of aneurysm treatment.

Current treatment for both ruptured and unruptured aneurysms includes surgical clipping (exovascular therapy) and catheter based intervention (endovascular therapy). The latter includes the placement of platinum coils or liquid gels into the aneurysm to arrest blood flow within the aneurysm sac and induce thrombosis of the lesion and its subsequent exclusion from the native circulation and/or placement of stent like devices across the aneurysm neck to achieve similar results. Some aneurysms are more amenable to one therapy or the other. Randomized controlled studies have shown that when aneurysms are judged to be good candidates for either therapy, endovascular therapy leads to better neurologic outcomes.

The primary downsides to endovascular aneurysm therapy are the risk of aneurysm recurrence and subsequent lesion rupture or re-rupture. While recurrence is possible when any aneurysm is treated endovascularly, the increased likelihood of such an event is directly proportional to increased aneurysm size, increase volume of pre-therapy intra-aneurysmal thrombus, and low fundus to neck ratio (fundal diameter primarily in the non-Z plane divided by the aneurysm neck diameter). These different criteria affect the surgeon's ability to densely fill the aneurysm with coil material so that coil compaction into the aneurysm's dome is limited. Such compaction is caused by a combination of arterial blood pressure pulsations which force the coil loops to densely collapse on one another thus opening up new space in the aneurysm dome and by intra-aneurysmal thrombolysis which reduces the ability for thrombus within the aneurysm to organize and support the coil mass against collapse into the aneurysm dome.

In an attempt to reduce the incidence of aneurysm recurrence following endovascular coiling, manufacturers have made several attempts to modify the platinum coil surface, coil shape/geometry, and coil stiffness. These modifications all seek to induce the holy grail of endovascular aneurysm therapy, maximization of coil pack density within the aneurysm (close to or greater than 35% of total aneurysm volume filled with coil material) and subsequent exclusion of the aneurysm neck from the native circulation and parent vessels by the induction of an endothelial layer that covers the interface between the coil material in the aneurysm neck and the parent vessel lumen and arterial blood flow. It is the growth of this endothelial layer that seals the aneurysm off from the normal arterial blood flow thus eliminating the risk of aneurysm recurrence.

While all coil manufacturers have altered their product's geometry and stiffness in an attempt to maximize coil density within the aneurysm fundus, only two manufacturers have altered their coil surfaces and studied the consequences of such alterations on aneurysm recurrence and endothelialization. Reinges et al. (*Bare, Bio-Active and Hydrogel-Coated Coils for Endovascular Treatment of Experimentally Induced Aneurysms: Long-Term Histological and Scanning Electron Microscopy Results*. Interventional Radiology, 2010. 16(2): p. 139-150) studied the different outcomes after coiling of experimental aneurysm using, unmodified platinum coils, hydrogel coated coils (HydroCoil, Microvention Therapeutics), and bioactive coils coated with PLGA copolymers (Matrix Coil, Boston Scientific, Fremont, Calif.). The premise behind hydrogel coating is that once the coil is inserted into the aneurysm the hydrogel swells, thus increasing the density of material within the aneurysm fundus and increasing the surface area of material at the neck of the aneurysm. These two effects of the coating presumably facilitate improved endothelial growth across the aneurysm neck and subsequent aneurysm exclusion from the native circulation. The premise behind the PLGA coating of bioactive coils is for the PLGA to produce an inflammatory reaction within the aneurysm and at the neck of the aneurysm thus enhancing clot organization and maturation and accelerating neointimal proliferation. The authors found that PLGA provided no benefits compared to bare platinum coils. Hydrogel coils increased the likelihood of intraneurysmal fibrosis along with instances of neoendothelial proliferation and endothelial spanning of tissue from one coil loop to another leading to neck coverage. Murayama et al. (*Ion implantation and protein coating of detachable coils for endovascular treatment of cerebral aneurysms: concepts and preliminary results in swine models*. Neurosurgery, 1997. 40(6): p. 1233-43; discussion 1243-4) also looked to alter platinum coils using ion implantation and protein coating with fibronectin. They found greater fibrous coverage of the aneurysm necks in the modified coils group compared to the bare platinum treated animals. These experimental results have been partially confirmed by clinical studies. Piotin et al. (*Intracranial Aneurysms Coiling With Matrix: Immediate Results in* 152 *Patients and Mid-term Anatomic Follow-Up From* 115 *Patients*. Stroke, 2009. 40(1): p. 321-323) found that Matrix coils provided no improvement in aneurysm recanalization rates compared to bare platinum coils.

Once an aneurysm is filled with coils, the influx of pulsating blood is reduced as hemodynamic pressure is distributed and absorbed by the coil mass. Intraneurysmal blood flow becomes turbulent and the process of coagulation can begin (Piotin, M., et al., *Intracranial Aneurysms Coiling with Matrix: Immediate Results in* 152 *Patients and Midterm Anatomic Follow-Up From* 115 *Patients*. Stroke, 2009. 40(1): p. 321-323). Histologic studies have shown that following coil placement in an aneurysm dome, platelets and fibrin deposit on the coil's loops. Over time the fibrin clot organizes and granulation tissue forms between the coil loops thus stabilizing them. This tissue forms a matrix over which neoendothelial cells, which emerge from the sur- rounding healthy vessel wall, can gradually grow from the periphery to eventually cover the portion of the coils exposed to the arterial blood flow in the parent vessel's lumen. In the ideal situation, this neoendothelial layer effectively isolates the aneurysm from the arterial blood flow eliminating the risk of subsequent aneurysm recanalization, recurrence, and rupture. However, the rate at which a complete neoendothelial layer forms is currently unknown. Literature suggests that after 5 days of coil deposition a thrombus consisting of erythrocytes and fibrin are found throughout the dome. Within 2 weeks foamy macrophages are found near the coils and by 270 days scar formation with vascularized connective tissue surrounds the coils and fills the fundus while endothelial cells seal the aneurysm neck. It is the surgeon's hope that this process can occur as quickly and reliably as possible since an ideal outcome is contingent upon the completion of this process.

Histologic findings following the use of hydrogel coated coils suggest that this material might enhance neoendothelial sealing of the aneurysm by promoting thrombosis through a more dense aneurysm fill and by presenting a greater surface are at the neck over which neoendothelial cells can sprout and spread to form a contiguous membrane. While the use of hydrogel coatings may seem attractive, a subset of patients who underwent HydroCoil implantation have developed delayed aseptic meningitis, intraparenchymal cyst formation, and hydrocephalus. It is unclear whether or not higher rates of aneurysm occlusion justify such potential complications.

SUMMARY

The methods and devices described herein are useful in the treatment of aneurysms. A vaso-occlusive device, such as an embolism coil is provided comprising a coating that incorporates, e.g., by mixing, genipin or a crosslinking genipin derivative, inclusive of pharmaceutically acceptable salts thereof, with the polymer during coating of the coil, or by absorption and/or adsorption of the genipin to the polymer. Genipins act as cross-linking agents, thereby increasing stability of clots within the aneurysm by cross-linking fibrin and/or other compositions comprising primary amines. According to one non-limiting embodiment, the polymeric coating is a bioerodible polymer such as poly(L-lactide-co-glycolide) (PLGA), comprising genipin. Dissolution of the polymeric coating and/or elution of incorporated genipin results in release of genipin over time to crosslink fibrin clots, thereby creating a more stable occlusion. Furthermore, this solution permits accelerated healing and remodeling of the vasculature and therefore is likely to solve many of the problems with current treatments based on endovascular coiling. Genipin is a naturally occurring compound that is cost-effective, easy to handle, and has been used in other food and medical products. Taken together, the described methods and devices have the possibility for revolutionizing endovascular coiling treatment of intracranial aneurysms.

Accordingly in one embodiment of the methods provided herein, a method of treating an aneurysm in a patient is provided. The method comprises feeding (that is, introducing, placing, etc.) a vaso-occlusive device and genipin or a crosslinking genipin derivative into a fundus of the aneurysm using a catheter. In one embodiment, the genipin or a crosslinking genipin derivative is incorporated into a bioerodible polymer. In another embodiment, the vaso-occlusive device, such as an embolism coil, comprises a core substrate and a controlled release coating layer on the core substrate comprising the genipin or a crosslinking genipin derivative. In one embodiment, the controlled release coating layer comprises genipin or a pharmaceutically acceptable salt thereof. In another embodiment, the controlled release coating layer comprises a crosslinking derivative of genipin or a pharmaceutically acceptable salt thereof. In one particular embodiment, crosslinking derivative of genipin is a compound according to formula 2 or a stereoisomer or pharmaceutically acceptable salt thereof:

where R1 is —H, =O or —OR4, where R4 is —H, $C_{1-6}$ alkyl, $C_{1-3}$ alkyl, or $C_{1-12}$ alkanoyl which can be substituted with phenyl, phenoxy, pyridyl or thienyl; R2 is H, $C_{1-6}$ alkyl, $C_{1-3}$ alkyl, methyl, ethyl, propyl, isopropyl, butyl, n-butyl, t-butyl, isobutyl, or sec-butyl; and R3 is a primary alcohol chosen from —CH$_2$—OH and —R5-CH$_2$—OH, where —R5- is $C_{1-6}$ alkyl, $C_{1-3}$ alkyl, methyl, ethyl, propyl, isopropyl, butyl, n-butyl, t-butyl, isobutyl, or sec-butyl, other than genipin. In one embodiment, R1 is —OR4, where R4 is —H or $C_{1-3}$ alkyl. In another embodiment, R2 is H or $C_{1-3}$ alkyl and/or R3 is —CH$_2$—OH, —CH$_2$—CH$_2$—OH, or —CH$_2$—CH$_2$—CH$_2$—OH. In yet another embodiment, R2 is H or $C_{1-3}$ alkyl. In another embodiment, R3 is —CH$_2$—OH, —CH$_2$—CH$_2$—OH, or —CH$_2$—CH$_2$—CH$_2$—OH. In a further embodiment, the device comprises between the core substrate and the controlled release coating layer a polymeric intermediary layer, which is optionally a hydrogel. According to one embodiment, the controlled release coating layer is a bioerodible polymer comprising the genipin or crosslinking genipin derivative. Non-limiting examples of a bioerodible polymer are: a polyester, a polyester-containing copolymer, a polyanhydride, a polyanhydride-containing copolymer, a polyorthoester, and a polyorthoester-containing copolymer. In one embodiment, the polyester or polyester-containing copolymer is a poly(lactic-co-glycolic) acid (PLGA) copolymer. In another embodiment, the bioerodible polymer is selected from the group consisting of poly(lactic acid) (PLA); poly(trimethylene carbonate) (PTMC); poly(caprolactone) (PCL); poly(glycolic acid) (PGA); poly(glycolide-co-trimethylenecarbonate) (PGTMC); poly(L-lactide-co-glycolide) (PLGA); poly-ethylene-glycol (PEG-) containing block copolymers; and polyphosphazenes. In one embodiment, the controlled release coating layer is a non-bioerodible polymer comprising the genipin or crosslinking genipin derivative.

In another embodiment, a vaso-occluding catheter device is provided. The vaso-occluding catheter device comprises a sheath and a filament within the sheet, the filament comprising a core substrate and a controlled release coating layer on the core substrate comprising genipin or a crosslinking genipin derivative. In one embodiment, the core substrate is a metal, non-limiting examples of which include platinum, a platinum alloy or nitinol. In one embodiment, the controlled release coating layer comprises genipin or a pharmaceutically acceptable salt thereof. In another embodiment, the controlled release coating layer comprises a crosslinking derivative of genipin or a pharmaceutically acceptable salt thereof. Examples of the crosslinking genipin derivative include, without limitation, is a compound according to formula 2 or a stereoisomer or pharmaceutically acceptable salt thereof:

where R1 is —H, =O or —OR4, where R4 is —H, $C_{1-6}$ alkyl, $C_{1-3}$ alkyl, or $C_{1-12}$ alkanoyl which can be substituted with phenyl, phenoxy, pyridyl or thienyl; R2 is H, $C_{1-6}$ alkyl, $C_{1-3}$ alkyl, methyl, ethyl, propyl, isopropyl, butyl, n-butyl, t-butyl, isobutyl, or sec-butyl; and R3 is a primary alcohol chosen from —$CH_2$—OH and —R5-$CH_2$—OH, where —R5- is $C_{1-6}$ alkyl, $C_{1-3}$ alkyl, methyl, ethyl, propyl, isopropyl, butyl, n-butyl, t-butyl, isobutyl, or sec-butyl, other than genipin. In one example, R1 is —OR4, where R4 is —H or $C_{1-3}$ alkyl. In another example, R2 is H or $C_{1-3}$ alkyl and/or R3 is —$CH_2$—OH, —$CH_2$—$CH_2$—OH, or —$CH_2$—$CH_2$—$CH_2$—OH. In yet another example, R2 is H or $C_{1-3}$ alkyl. In yet another example, R3 is —$CH_2$—OH, —$CH_2$—$CH_2$—OH, or —$CH_2$—$CH_2$—$CH_2$—OH. The device optionally comprises between the core substrate and the controlled release coating layer a polymeric intermediary layer, such as a hydrogel. In one embodiment, the controlled release coating layer is a bioerodible polymer comprising the genipin or crosslinking genipin derivative. Non-limiting examples of a bioerodible polymer are: a polyester, a polyester-containing copolymer, a polyanhydride, a polyanhydride-containing copolymer, a polyorthoester, and a polyorthoester-containing copolymer. In one embodiment, the polyester or polyester-containing copolymer is a poly(lactic-co-glycolic) acid (PLGA) copolymer. In another embodiment, the bioerodible polymer is selected from the group consisting of poly(lactic acid) (PLA); poly(trimethylene carbonate) (PTMC); poly(caprolactone) (PCL); poly(glycolic acid) (PGA); poly(glycolide-co-trimethylenecarbonate) (PGTMC); poly(L-lactide-co-glycolide) (PLGA); polyethylene-glycol (PEG-) containing block copolymers; and polyphosphazenes. In one embodiment, the controlled release coating layer is a non-bioerodible polymer comprising the genipin or crosslinking genipin derivative.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

Described herein are methods of treating aneurysms and devices useful in treating aneurysms. The methods employ a vaso-occlusive device that is catheter-deployed, such as an embolism coil. The device comprises a vaso-occlusive device that incorporates slow-releasing genipin, or a crosslinking genipin derivative, including pharmaceutically acceptable salts thereof, as defined below and collectively referred to as "the compound". In further detail according to one embodiment, the device includes a filamentous substrate, typically metallic, coated with a polymer that includes the genipin. The polymer can be bioerodible, and if not, the compound diffuses from the polymer at a controlled rate. If the polymer is bioerodible, then the compound is released as the polymer erodes, and the erosion rate is determined by the polymer composition and can be tailored to erode over a time period extending from days to years. A polymer coating that does not contain, or substantially or essentially does not contain (e.g., it is prepared without drug product, but may contain drug product leached from another layer), drug product can be used to either coat the drug-containing layer, or be placed as an intermediary layer between the drug-containing layer and the underlying, typically metallic, substrate.

As used herein, the term "polymer" in general includes, for example and without limitation, homopolymer(s), copolymer(s), polymeric blend(s), block polymer(s), block copolymer(s), cross-linked polymer(s), non-cross-linked polymer(s), linear-, branched-, comb-, star-, and/or dendrite-shaped polymer(s), where polymer(s) can be formed into any useful form, for example and without limitation, a hydrogel, a porous mesh, a fiber, woven mesh, or non-woven mesh, such as, for example and without limitation, a non-woven mesh formed by electrospinning.

Figure 1:
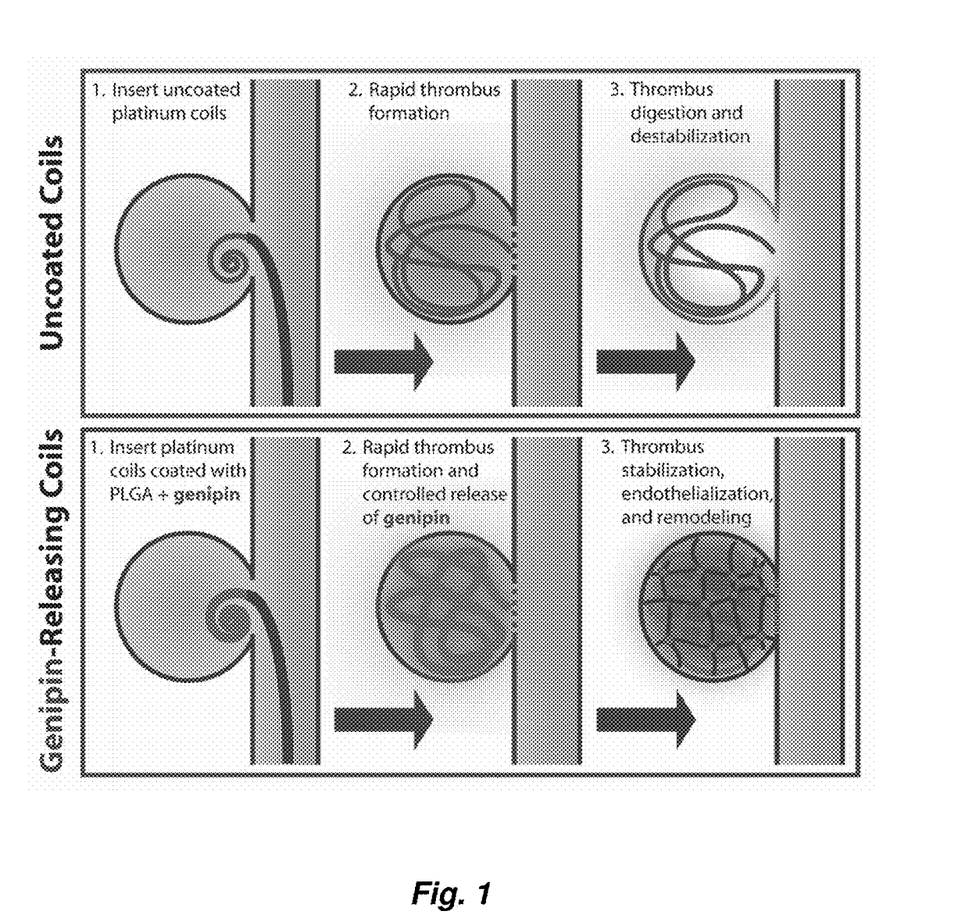
FIG. 1 depicts one embodiment for use of genipin- or crosslinking genipin derivative-releasing coils for the improved treatment of aneurysms.

FIG. 1 provides a non-limiting embodiment of the disclosed methods and devices. Currently available therapies include uncoated platinum coils, shown in the top panel. In that approach, (1) platinum coils are inserted into the fundus of the aneurysm (e.g., D~5 mm). (2) The presence of these coils induces clotting and eventual compaction to fill the void. (3) However, over time the nascent clot can be cleaved by fibrolytic/thrombolytic enzymes, which ultimately leads to digestion and destabilization of the clot. The ultimate mode of failure is recanalization in which the occlusion is opened up again. The approach described herein aims to use coils that release genipin or crosslinking derivatives thereof. Genipin is a naturally-occurring compound that can induce protein crosslinking via the formation of stable covalent bonds. Embolism coils are coated with a coating that can deliver genipin in a controlled release manner. As shown in FIG. 1, bottom panel: (1) first, standard coil materials (i.e. platinum) are coated with a matrix of poly(L-lactide-co-glycolide) that is loaded with genipin; (2) the insertion of these coils leads to rapid thrombus formation and simultaneous release of genipin into the aneurysm, and (3) the bioactive genipin then crosslinks the nascent clot with a unique covalent chemistry that is resistant to proteolysis. The crosslinked fibrin clot is then stabilized, which can reduce the risk of recanalization and is expected to allow broader timelines for endothelialization, remodeling, and closure of the aneurysm.

In one embodiment, a bioactive coil is developed that can promote aneurysm thrombosis and neoendothelial sealing of the aneurysm fundus. The novel method utilizes platinum coils that are coated with a polymer matrix that can control the local release of, for example, genipin, or a derivative thereof into the aneurysm. Genipin (Formula 1, methyl (1S,2R,6S)-2-hydroxy-9-(hydroxymethyl)-3-oxabicyclo [4.3.0]nona-4,8-diene-5-carboxylate, CAS No. 6902-77-8) is a naturally occurring compound that is found in the fruit of the *Gardenia jasminoides*.

1

This bioactive compound can crosslink extracellular matrix molecules through the formation of stable covalent crosslinks that are resistant to enzymatic degradation (Bigi, A., et al., *Stabilization of gelatin films by crosslinking with genipin*. Biomaterials, 2002. 23(24): p. 4827-4832; Chang, Y., et al., *Acellular bovine pericardia with distinct porous structures fixed with genipin as an extra cellular matrix*. Tissue Enginering, 2004. 10(5-6): p. 881-892; Liang, H.-C., et al., *Effects of crosslinking degree of an acellular biological tissue on its tissue regeneration pattern*. Biomaterials, 2004. 25(17): p. 3541-3552; Sung, H.-W., et al., *Crosslinking of biological tissues using genipin and/or carbodiimide*. Journal of Biomedical Materials Research Part A, 2003. 64A(3): p. 427-438; and Sung, H.-W., et al., *Stability of a biological tissue fixed with a naturally occurring crosslinking agent (genipin)*. Journal of Biomedical Materials Research, 2001. 55(4): p. 538-546). Genipin stabilizes the formation of crosslinked gels based on biopolymers that have amino acid residues with pendant primary amines such as aspargine (Asp, N), glutamine (Gln, Q), lysine (Lys, K), and arginine (Arg, R). This mechanism has been used to form mechanically robust gels from gelatin and collagen (Bigi, A., et al., *Stabilization of gelatin films by crosslinking with genipin*. Biomaterials, 2002. 23(24): p. 4827-4832 and Sundararaghavan, H. G., et al., *Genipin-induced changes in collagen gels: Correlation of mechanical properties to fluorescence*. Journal of Biomedical Materials Research Part A, 2008. 87A(2): p. 308-320). Genipin can crosslink fibrin (See, e.g., United States Patent Publication No. 2012/0189584).

Chemical crosslinks generated by the incorporation of genipin render networks of extracellular matrices less susceptible to enzymatic degradation. For example, genipin has been shown to limit inflammation-mediated degradation of agarose gels when used in tissue engineering applications (Lima, E. G., et al., *Genipin enhances the mechanical properties of tissue-engineered cartilage and protects against inflammatory degradation when used as a medium supplement*. Journal of Biomedical Materials Research Part A, 2009. 91A(3): p. 692-700). In one example, genipin is used as a bioactive agent that can be leveraged to form a stable thrombus within the fundus of the aneurysm. Increased stability of the thrombus reduces the risk of enzyme-mediated recanalization, which is the primary mode of recurrence.

Genipin derivatives useful in the present invention include those with the ability to react with primary amines and thereby cross-link proteins, such as fibrin, comprising primary amines, which include amino acid residues of asparagine (Asp, N), glutamine (Gln, Q), lysine (Lys, K) or Arginine (Arg, R). In the context of the present disclosure, useful genipin derivatives have the ability to crosslink fibrin and are referred to herein as "crosslinking genipin derivatives". The disclosures of U.S. Pat. Nos. 5,272,172, 6,162,826, 6,262,083, and 7,649,014, each of which is incorporated herein by reference for the disclosure of genipin derivatives many or most of which are expected to include protein crosslinking activity. A "genipin derivative" is therefore either a compound designated as such herein, an iridoid derivative as disclosed in U.S. Pat. No. 5,272,172, or a genipin derivative disclosed in any one of U.S. Pat. Nos. 6,162,826, 6,262,083, and 7,649,014, and includes stereoisomers and pharmaceutically acceptable salts thereof. Crosslinking activity for any given compound is easily determined by a person of ordinary skill by mixing a primary-amine-containing protein, such as fibrin with the candidate compound and determining by any of a large number of available physical, chemical or optical assays whether or not the compounds are cross-linked. An Example of a useful crosslinking assay is described in U.S. Pat. No. 7,649,014 (column 38), where genipin forms a dark blue pigment when crosslinked by an amine nucleophile, such as: primary amines such as methylamine; amino acids; and peptides.

U.S. Pat. No. 7,649,014 provides one criterion for distinguishing cross-linking genipin derivatives from non-crosslinking genipin derivatives. Without intent of being bound to this theory, in crosslinking genipin derivatives, primary amines replace the oxygen of the 3-oxane of genipin and its derivatives and the C8-C9 double bond and the C9 primary alcohol appear to be required for crosslinking (See, FIG. 2). To avoid confusion, numbering of the genipin structure, and genipin derivatives is in reference to the structure above, and not to the numbering of any cited reference. Therefore, based on the disclosures of U.S. Pat. Nos. 5,272,172, 6,162,826, 6,262,083, and 7,649,014, each of which is incorporated herein by reference for the disclosure of genipin derivatives and methods of making genipin and genipin derivatives, exemplary crosslinking genipin derivatives include compounds of the following formula 2, and stereoisomers and pharmaceutically acceptable salts thereof:

2

In formula 2, R1 is —H, =O or —OR4, where R4 is —H, $C_{1-6}$ alkyl, $C_{1-3}$ alkyl, methyl, ethyl, propyl, isopropyl, butyl, n-butyl, t-butyl, isobutyl, sec-butyl, propylbenzyl, or $C_{1-12}$ alkanoyl which can be substituted with phenyl, phenoxy, pyridyl or thienyl. R2 is H, $C_{1-6}$ alkyl, $C_{1-3}$ alkyl, methyl, ethyl, propyl, isopropyl, butyl, n-butyl, t-butyl, isobutyl, or sec-butyl. R3 is a primary alcohol chosen from —$CH_2$—OH and —R5-$CH_2$—OH, where —R5- is $C_{1-6}$ alkyl, $C_{1-3}$ alkyl, methyl, ethyl, propyl, isopropyl, butyl, n-butyl, t-butyl, isobutyl, or sec-butyl. As an example, for genipin: R1 is —OH, R2 is methyl, and R3 is —$CH_2$—OH.

Figure 2:
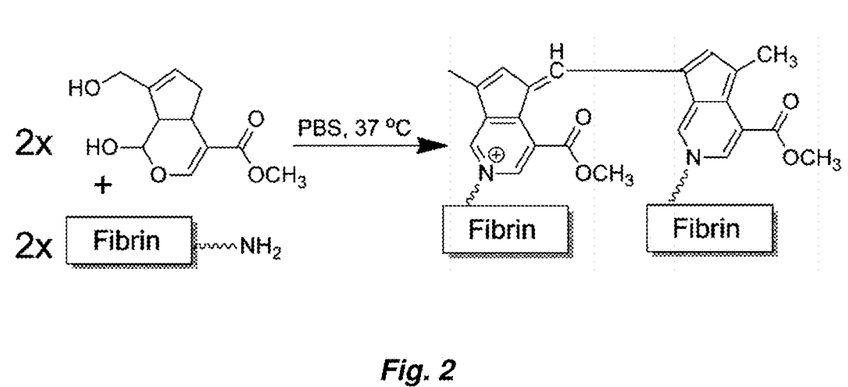
FIG. 2 illustrates a mechanism for genipin crosslinking of proteins.

FIG. 2 illustrates a mechanism for Genipin Crosslinking of Proteins. Primary amines in virtually any protein (collagen, fibrin, gelatin, etc.) react with two genipin molecules to produce a covalent crosslink. The source of these amines arises from amino acid residues such as aspargine (Asp, N), glutamine (Gln, Q), lysine (Lys, K), and arginine (Arg, R). Two genipin molecules are consumed to form one covalent crosslink between two residues. Furthermore, the molecular signature of this crosslink is widely resistant to degradation from fibrolytic and thrombolytic enzymes. This type of covalent crosslinking is well-suited to stabilize nascent fibrin clots that are formed within intracranial aneurysms.

Butler et al. ("Mechanism and Kinetics of the Crosslinking Reaction between biopolymers Containing Primary Amine Groups and Genipin,"*J. Polymer Science: Part A Polymer Chemistry* (2003) 41:3941-3953) provides a different mechanism, including two alternate pathways, one implicating the ester group at the 5 position and the other, as an alternate to the mechanism described above, involving C4, O3 and R1, wherein R1 is OH in one embodiment. Irrespective of the mechanism of crosslinking, the compounds meeting the requirements of formula 2 are expected to crosslink primary amine-containing compounds. The cross-linking functionality of genipins are active with respect to a variety of biological macromolecules, such as fibrin and heparin, with excellent biocompatibility. See, e.g., Tsai, C., et al., "Effects of Heparin Immobilization on the Surface Characteristics of a Biological Tissue Fixed with a Naturally Occurring Crosslinking Agent (Genipin): an In Vitro Study," (2001) *Biomaterials* 22:523-533).

As used herein, "genipin and crosslinking genipin derivatives" comprise pharmaceutically acceptable salts of genipin and the crosslinking genipin derivatives. A "pharmaceutically acceptable salt" as used herein is intended to mean an active ingredient (drug) comprising a salt form of any compound as described herein. The salt form typically confers to the improved and/or desirable pharmacokinetic/pharmodynamic properties of the compounds described herein, so long as crosslinking is not affected. Pharmaceutically acceptable salts of any of the compounds described herein also may be used in the methods described herein. Pharmaceutically acceptable salt forms of the compounds described herein may be prepared by conventional methods known in the pharmaceutical arts, and include as a class veterinarily acceptable salts. For example and without limitation, where a compound comprises a carboxylic acid group, a suitable salt thereof may be formed by reacting the compound with an appropriate base to provide the corresponding base addition salt. Non-limiting examples include: alkali metal hydroxides, such as potassium hydroxide, sodium hydroxide and lithium hydroxide; alkaline earth metal hydroxides, such as barium hydroxide and calcium hydroxide; alkali metal alkoxides, such as potassium ethanolate and sodium propanolate.

As used herein, a "vaso-occlusive device" refers, in one embodiment, to an elongate, flexible wire or filament prepared, for example and without limitation from coiled metal, such as platinum or an alloy thereof, commonly used in the endovascular treatment of aneurysms, for example and without limitation by filling the dome or fundus of a saccular aneurysm. Such vaso-occlusive devices are often referred to as "embolism coils." Stents are often used for repair of fusiform aneurysms. Many versions of this device are available commercially, and they include non-coated (bare) metal devices and devices comprising coatings or other modifications, such as inclusion of non-metal filaments. A common embodiment of a vaso-occlusive device is known as a Guglielmi detachable coil. As non-limiting examples of vaso-occlusive devices, U.S. Pat. Nos. 7,896,899 and 8,273,100 depict bare metal devices as well as devices including filaments incorporated within the metal structure and hydrogel coatings. The filaments of the vaso-occlusive devices may be designated as "framing" or "finishing" or "filling" in that some are used to create the framework of the coiled mass within the aneurysm, while others are "softer" being more flexible and often including a hydrogel coating, and are used to fill the aneurysm. In one embodiment a "framing" coil is prepared from a shape memory alloy, such as nitinol, and optionally is pre-shaped prior to deployment, in the shape of a dome, sac or fundus of a saccular aneurysm. A typical and non-limiting vaso-occlusive device is a flexible filament formed from a metal coil, braid, cut cylinder, etc. As is well-known in the art, a multitude of alternate configurations for the vaso-occlusive device, or embolism coil are known, and are modifiable according to the methods described herein. In the context of the methods and devices described herein, the configuration of the underlying vaso-occlusive structure is not material so long as it can be modified to release genipin and derivatives thereof useful in the methods. Although depicted as a filament, other shapes are capable of deployment by a catheter in endovascular methods, and any structure useful for vascular occlusion can be used as a core structure that may be modified to include elutable genipin or crosslinking genipin derivatives.

As would be recognized by those of ordinary skill, methods of treating an aneurysm include not only use of a coated embolism coil, but concurrent deployment of genipin or a crosslinking genipin derivative as described herein with a standard embolic coil. The genipin or crosslinking genipin derivative is preferably incorporated into a catheter-deployable slow-release dosage form, such as, without limitation, a bioerodable polymer filament prepared from a bioerodible polymer according to any embodiment as described herein in the context of the controlled release coating layer. The controlled release dosage form is deployed in the aneurysm fundus with, for example, an embolism coil and stabilizes a clot formed within the aneurysm. For example, a fiber is prepared from PLGA, containing an amount of genipin or a crosslinking genipin derivative effective to release in a 1 mL fundus or 1 mL of an aqueous solvent of between 1 ng and 100 μg of the genipin or a crosslinking genipin derivative per day. The fiber is deployed into a fundus of an aneurysm by a catheter before, during, or after deployment of an embolism coil within the fundus. In one example, the fiber is wrapped about (around and/or intertwined with) an embolism coil.

Vaso-occlusive devices are typically deployed in an endovascular catheter or microcatheter device as are broadly know in the arts for deployment of such vaso-occlusive devices and stents. Common metals used in the manufacture of such devices are biocompatible and preferably radiodense (e.g., radiopaque), permitting visualization during deployment. Metals used in vaso-occlusive devices include: platinum, tantalum, iridium, tungsten, gold, titanium, and alloys thereof, such as nitinol and Elgiloy (Co—Cr—Ni). Alloys comprising a predominance of platinum, such as platinum-iridium or platinum-tungsten alloys are common.

Figure 3A:
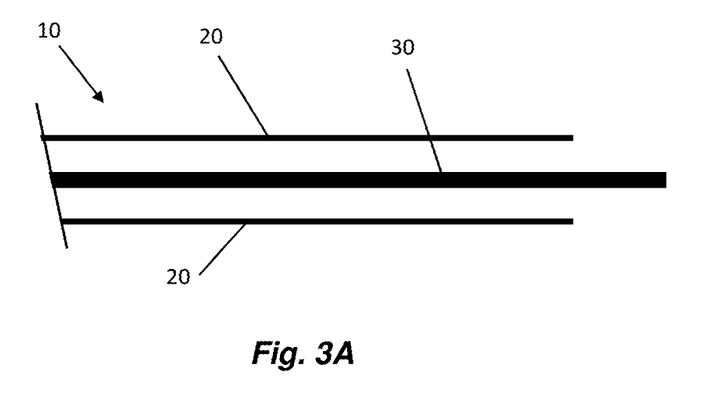
FIGS. 3A-3D depict non-limiting embodiments of a vaso-occlusive device as described herein.
Figure 3B:
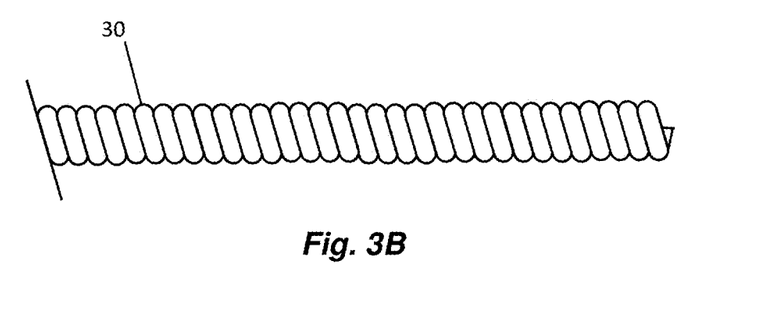
Figure 3C:
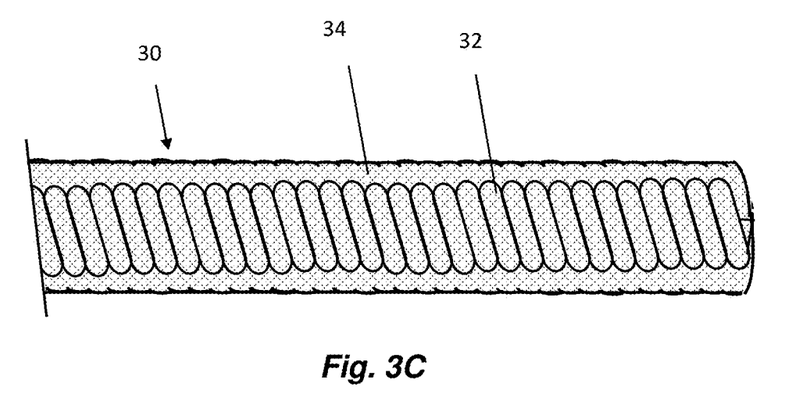
Figure 3D:
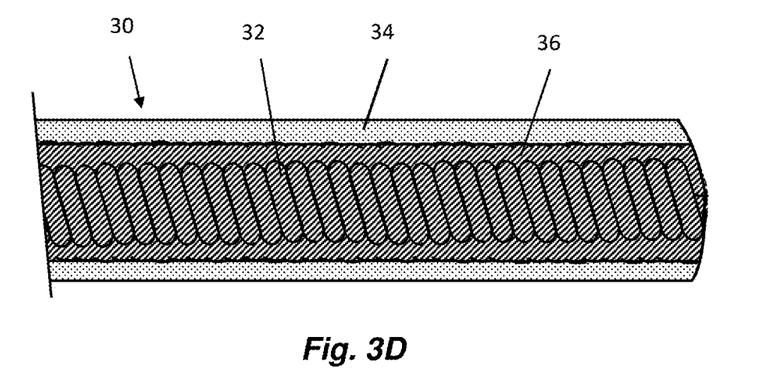

FIG. 3A depicts schematically in cross section a simplified catheter structure for deploying a vaso-occlusive filament. Catheter 10, or microcatheter, comprises a sheath 20 and a filament 30. FIG. 3A depicts only a distal terminal end (away from a user of the device) of a catheter device, with the slash at left indicating that the catheter structure continues. The proximal end of the catheter 10, including any control structures for manipulation of the filament 30 or other features of the catheter that are not depicted for ease of understanding, is not shown. FIGS. 3B, 3C and 3D depict schematically variations in structure of the filament 30 depicted in FIG. 3A. Although FIGS. 3B-3D show a helical coil structure, a very common structure to many embodiments of the filaments of vaso-occlusive devices, the helical coil structure is a non-limiting example provided for illustrative purposed only, and the filament can have any structure, such as a braided structure or more complex configurations disclosed for example and without limitation in U.S. Pat. Nos. 7,896,899 and 8,273,100.

FIG. 3B shows schematically a bare metal filament 30, depicted for illustration purposes only as a helical metal coil. FIG. 3C shows schematically a filament 30 comprising a core 32, depicted for illustration purposes only as a helical metal coil, and a polymeric coating 34 comprising elutable genipin or a derivative thereof, indicated by speckling in the coating 34. FIG. 3D depicts schematically an alternate embodiment of the filament 30 depicted in FIG. 3A. Filament 30 comprises a core 32, as in FIG. 3C, and a coating 34 comprising elutable genipin or a crosslinking genipin derivative, and further comprises a polymeric intermediary layer 36 between the core 32 and the polymeric coating 34. In one non-limiting embodiment, the coating 34 comprises a bioerodible polymer, while intermediary layer 36 comprises a polymer, such as a swellable hydrogel as are known in the field of vaso-occlusive devices. In one embodiment, the intermediary layer erodes more slowly than the polymeric coating 34. Alternate materials can be used as an alternative to metals in the filament 30 of FIG. 3B and core 32 of FIGS. 3C and 3D, such as biocompatible polymer structures having the desired flexibility. In many instances, however, metal is preferred for use in the device for the core. For ease of description, the core 32 is referred to as a "core substrate."

In an alternate version of the device, and referring to FIG. 3D for context, the polymeric coating 34 does not contain drug, but can be erodable or non-erodable and the polymer is porous or non-porous. The intermediary layer 36 is a polymeric substrate comprising the genipin or crosslinking genipin derivative, and the polymeric coating controls diffusion of the drug from the intermediary layer and therefore from the device.

Vaso-occlusive devices are also broadly commercially available from many sources including: Codman & Shurtleff, Inc. of Raynham, Masachusetts (CASHMERE®, CERECYTE®, DELTAMAXX®, DELTAPAQ® and DELTAPLUSH® microcoils); Covidien/ev3 Endovascular of Plymouth, Minn. (AXIUM™ detachable coil system); MicroVention, Inc. of Tustin, Calif. (MICROPLEX®, COSMOS®; HYPERSOFT® HYPERSOFT® 3D, and COMPASS® coils); Stryker Neurovascular of Fremont, Calif. (TARGET® and GDC 360°® coils). Some of these devices are "bare coil" devices as shown in FIG. 3B, while others, often designated as "finishing coils" and the like, include a hydrogel as in FIG. 3C, but not including genipin or a derivative thereof. These commercially-available devices can be modified by adding a controlled release genipin or genipin derivative element as described herein.

Genipin or a crosslinking genipin derivative ("the compound") is incorporated into the structure of a vaso-occlusive device, such as a filament or an embolism coil so that the compound is released over an extended period of time that typically ranges from one day to several months or longer, including increments therebetween. In one embodiment, the genipin is absorbed into, mixed with or attached to a coating on an embolism coil. In one embodiment, the compound is mixed with a polymeric coating material prior to application of the coating to a vaso-occlusive device, such as an embolism coil. In another embodiment, a vaso-occlusive device, such as an embolism coil is first coated with a polymeric coating and the compound is applied to the polymeric coating, resulting in absorption of the compound into the polymeric coating or adsorption onto the polymeric coating. Incorporation of an active agent, such as genipin or a derivative thereof is referred to as "loading." In one embodiment, the polymeric coating may be applied to a surface of the core substrate, for example by dipping or spraying (including electrospraying). The coating optionally is porous, as in a foam.

In another embodiment, the coating is applied as one or more fibers wound about (onto and/or into) the core substrate. Winding a fiber "within" the core substrate recognizes that many such core substrates are coils that include gaps between turns that exist in a relaxed state of the coil, or when the coil is stretched, and the fibers can be wound between adjacent turns of the core substrate. The fibers can be loaded with genipin or a derivative thereof prior to incorporation into the filament structure, or the fibers can first be incorporated into the filament structure and subsequently loaded. Filaments can be wound in a regular pattern about (around and/or within) a core substrate, or irregularly, as in a fiber mat, for example that is electrodeposited onto the core substrate.

As indicated above, genipin or a crosslinking genipin derivative is elutable from the vaso-occlusive device, meaning that the compound can freely diffuse from the structure in an aqueous medium such as, without limitation, water, saline, PBS (phosphate-buffered saline), blood or plasma such that the compound is released from the core substrate. The compound is not immediately releasable, meaning that the compound is not released as a single bolus upon exposure to blood. One reason for the undesirability of immediate release is to avoid release of the compound into the bloodstream, as genipin is known to have systemic effects. A number of mechanisms for slow or extended release of compounds are known.

A first method of extending the release profile of the compound is to incorporate the compound in a slowly-dissolving biocompatible substance on the core substrate, such that the compound is released into the bloodstream as the slowly-dissolving substance dissolves/erodes. In use, the compound is mixed into the slowly-dissolving substance and upon contact with the blood in the aneurysm, the slowly-dissolving substance dissolves, releasing the compound. Carrier systems for slow release are known in the compounding arts, and many are suitable for use in implants. Exemplary compositions typically include excipients such as, without limitation: magnesium stearate, a polyethylene glycol (PEG), glycerol, cellulose or cellulose derivatives, such as microcrystalline cellulose or carboxymethylcellulose, a non-ionic detergent such as TWEEN®, and sugars, such as lactose, and mixtures thereof. Suitable candidates for slowly-dissolving substance include small molecules with a molecular weight below 2000 g/mol. These are incorporated into or onto the device by any suitable process, such as by drying a slurry or melt of the mixture onto the device.

A second method for the slow deployment of the genipin or crosslinking genipin derivatives is to absorb or adsorb the compound into and/or onto a coating of the device. The coating can be a microporous or non-porous structure, optionally including a drug-free top coat, prepared, for example, from a polymer, such as, without limitation, silicone or polysiloxanes, polyurethane, poly(ether urethane) urea, polyacrylates or PTFE (polytetra-fluoroethylene). In one non-limiting example, the composition is a blend (e.g., 67% to 33%) of poly(ethylene-co-vinyl acetate) and poly (n-butyl methacrylate) (PEVA-PBMA). A drug-free top layer or top coat of PBMA, or any suitable polymer also can be added to function as a barrier through which drug elutes out under diffusion, thereby further controlling the rate of release. In another non-limiting embodiment, poly(styrene-b-isobutylene-b-styrene), or SIBS, a hydrophobic triblock copolymer composed of styrene and isobutylene units built on 1,3-di(2-methoxy-2-propyl)-5-tert-butylbenzene, may be used to provide controlled, slow release of the compound. In yet another embodiment, vinylidene fluoride and hexafluoropropylene (PVDF-HFP) copolymer—an acrylic and fluoro copolymer made from vinylidene fluoride (VF) and hexafluoropropylene (HFP) monomers—is used to provide controlled release of the compound. Although the composition can be erodible in vivo, the mechanism of drug release is by diffusion.

A third method for slow deployment of the genipin or crosslinking genipin derivatives is to incorporate the compound into a biocompatible, bioerodible matrix. This is typically achieved by mixing the compound with a polymer solution prior to incorporation of the polymer solution into the vaso-occlusive device, or forming any other useful structure for delivery of the compound to the aneurysm fundus. The compound is eluted from the polymeric matrix by bioerosion and to some extent diffusion from the surface or from near the surface of the polymer. By "bioerodible," it is meant that a polymer, once implanted and placed in contact with bodily fluids and/or tissues, will degrade either partially or completely through chemical, biochemical and/or enzymatic processes. Non-limiting examples of such chemical reactions include acid/base reactions, hydrolysis reactions, and enzymatic cleavage. In certain non-limiting embodiments, the biodegradable polymers may comprise homopolymers, copolymers, and/or polymeric blends comprising, without limitation, one or more of the following monomers: glycolide, lactide, caprolactone, dioxanone, and trimethylene carbonate. In other non-limiting embodiments, the polymer(s) comprise labile chemical moieties, non-limiting examples of which include esters, anhydrides, or polyanhydrides, which can be useful in, for example and without limitation, controlling the degradation rate of the scaffold and/or the release rate of therapeutic agents from the scaffold.

The polymeric components used to make the bioerodible coating(s) are preferably biocompatible. By "biocompatible," it is meant that a polymer compositions and its normal degradation in vivo products are cytocompatible and are substantially non-toxic and non-carcinogenic in a patient within useful, practical and/or acceptable tolerances. By "cytocompatible," it is meant that the polymer can sustain a population of cells and/or the polymer composition, device, and degradation products thereof are not cytotoxic and/or carcinogenic within useful, practical and/or acceptable tolerances. For example, the polymer when placed in a human epithelial cell culture does not adversely affect the viability, growth, adhesion, and number of cells. In one non-limiting embodiment, the compositions and/or devices are "biocompatible" to the extent they are acceptable for use in a human or veterinary patient according to applicable regulatory standards in a given jurisdiction. In another example the biocompatible polymer, when implanted in a patient, does not cause a substantial adverse reaction or substantial harm to cells and tissues in the body, for instance, the polymer composition or device does not cause necrosis or an infection resulting in harm to tissues from the implanted scaffold.

Useful bioerodible polymeric compounds are known in the medical and pharmaceutical arts. Bioerodible polymers are polymers that are broken down over a desired time period. Among other factors, the composition of a polymer and the three-dimensional structure thereof will dictate the speed of erosion when implanted. Typical erosion times range from 24 hours up to two years and increments there between. In the context of the present disclosure, the erosion time for the coating containing the compound is from one week to two years, for example from two to six months. The polymer and the dissolution products thereof are biocompatible in that they do not cause or elicit unsafe or toxic effects when implanted. Suitable polymers are known in the medical arts, with polyesters being common in such applications. Polyesters include homopolymers and copolymers, including block copolymers, such as, without limitation: poly(lactic acid) (PLLA); poly(trimethylene carbonate) (PTMC); poly(caprolactone) (PCL); poly(glycolic acid) (PGA); poly(glycolide-co-trimethylenecarbonate) (PGTMC); poly(L-lactide-co-glycolide) (PLGA); polyethylene-glycol- (PEG-) containing block copolymers, such as PEG-PLGA-PEG or PEG-PLA-PEG block copolymers; and polyphosphazenes, such as polyorganophosphazenes. Non-erodable polymers either do not erode substantially in vivo or erode over a time period of greater than two years. Compositions such as, for example and without limitation, PTFE, poly(ethylene-co-vinyl acetate), poly(n-butylmethacrylate), poly(styrene-b-isobutylene-b-styrene) and polyethylene terephthalate are considered to be non-erodable polymers. Other suitable non-erodable polymer compositions are broadly known in the art, for example in stent coating and transdermal reservoir technologies.

The bioerosion profiles of copolymers and block copolymers can be altered by changing the relative ratio of monomers in the copolymer. For example and without limitation, the ratio of lactic acid to glycolic acid monomers incorporated into a PLGA composition with alter the bioerosion speed of the copolymer. As a consequence, useful PLGA composition comprise, in terms of molar quantities or number, from 1% to 99% lactic acid residues and from 99% to 1% glycolic acid residues (incorporated monomers of lactic acid or glycolic acid in the polymer), or molar feed ratios of 1% to 99% lactic acid and from 99% to 1% glycolic acid in the polymerization mixture, resulting in a similar molar ratio in the final product of respective residues. Other co-polymers, such as polyorganophosphazenes can be tailored for bioerosion duration accordingly.

Additional active agents may be incorporated into the device for release by any suitable method, such as those methods described above. These many include therapeutics such as, without limitation: antihypertensives, such as calcium channel blockers, for example and without limitation the dihydropyridines nimodipine and nifedipine, and beta blockers, such as propranolol. In another embodiment, a second small molecule crosslinking agent in addition to genipin or crosslinking derivatives thereof, such as glutaraldehyde, is incorporated into the device in non-toxic quantities, and is administered by the device according to the methods described herein.

It will be recognized that various combinations or layers of drug-containing and drug-free polymers may be combined to alter the release profile of the composition. For example a bioerodible layer may be placed above a non-erodible layer (See, e.g., FIG. 3D) such that drug is released over time, but a polymeric coating remains on the filament. Likewise a drug-free layer can overlay a drug-containing layer to regulate release of the drug by dissolution, determined, for example, by the thickness, permeability and porosity of the drug-free layer.

The polymer for the previous two embodiments in which the genipin is released by diffusion and/or erosion of a substrate may or may not comprise primary amines. If the polymer comprises primary amines, the genipin or cross-linking genipin derivative will crosslink the polymer, and the amount of compound used in the crosslinking would need to be accounted for in the product design. If primary amines are present in the polymer, then effective amounts of the genipin or crosslinking genipin derivative would need to be added above the amount of genipin incorporated into the polymeric structure via primary amines.

The field of coating stents and release of drugs from stents is well-developed, and the methods for delivering an active agent from the structure described herein in the context of occlusion of aneurysms by dissolution of a carrier substrate, by diffusion from a polymeric material or by bioerosion of a polymeric material, can be extended to the devices and methods described herein.

In an alternate embodiment, the compound can be introduced into the same location as the vaso-occlusive device during deployment of the device, but separately from the device. A slow-release drug product, in the form of a fiber or other structure, can be deployed into the desired location such as the sac of the aneurysm. The three-dimensional shape of the drug product is less material to the operability of this embodiment so long as the product can be deployed from a catheter into an aneurysm and can release the compound according to a useful profile. As a non-limiting example, a polymeric fiber prepared from a bioerodible, biocompatible (co)polymer (for example and without limitation, a polyester such as PLA, PGA or PLGA and other compositions described above and/or as are broadly known) and containing therein a safe and effective amount of the compound, can readily be deployed within an aneurysm.

In one embodiment, the treatment method is as follows. (1) First, standard coil materials (e.g., platinum or an alloy thereof) are coated with a matrix of poly(L-lactide-co-glycolide) that is loaded with genipin. (2) The insertion of these coils leads to rapid thrombus formation and simultaneous release of genipin into the aneurysm. (3) The bioactive genipin then crosslinks the nascent clot with a unique covalent chemistry that is resistant to proteolysis. The crosslinked fibrin clot is then stabilized which can reduce the risk of recanalization and will allow broader timelines for endothelialization, remodeling, and closure of the aneurysm.

In one embodiment, a method is used whereby controlled release strategy is integrated with platinum coils for delivering bioactive agents into the fundus of the aneurysm. Furthermore, an inert matrix based on PLGA method is used because PLGA is a material that is generally recognized as safe (e.g., GRAS material). Furthermore, there have been several pre-clinical and clinical trials that have deployed PLGA-based devices for use in treating intracranial aneurysms. PLGA is also a suitable matrix for the controlled release of small molecules including genipin. Genipin and PLGA share many common organic solvents and are compatible with many coating techniques that are based on solution-processing including acetone and dichloromethane. Sustained release of genipin into the nascent fibrin clots within the fundus may create a stable clot that is resistant to enzymatic degradation, remodeling, and recurrence via recanalization.

By the methods described herein, an organized thrombus is stabilized and remains localized within the coil interstices, the presence of this organized scar across the neck can produce a suitable matrix for cell migration. Specifically, the genipin-crosslinked proteins serve as a scaffold to enable efficient migration of neointimal cells from the surrounding vessels, which can grow and advance to cover and seal the aneurysm neck. In one example, genipin is safe for use in treating intracranial aneurysms given the extensive history of use as a bioactive compounds in other applications. While cytotoxicity studies have shown that this substance can cause cell death to L929 fibroblasts, these adverse effects are limited to exposures of 5 mM and 10 mM. For cross-linking purposes, cell samples incubated in 1 mM were indistinguishable from controls (Sundararaghavan, H. G., et al., *Genipin-induced changes in collagen gels: Correlation of mechanical properties to fluorescence. Journal of Biomedical Materials Research Part A*, 2008. 87A(2): p. 308-320.

As a consequence, the devices and methods described herein release a safe and effective amount of genipin or a crosslinking genipin derivative. By safe, it is meant a non-toxic amount of the compound, releasing the compound at a rate not to exceed an amount of genipin in the aneurysm fundus (typically less than 1 mL in volume) to exceed 5 mM (millimolar) and preferably less than 5, 4, 3, 2, 1, 0.5 or 0.1 mM. It should be noted that the packing of an aneurysm fundus requires variable amounts of vaso-occlusive filament. As such, the amount of the compound released per designated time period per unit length of the filament is most relevant. Elution profiles for any given filament can readily be determined empirically by submerging a fixed length of the filament in PBS or plasma and determining by e.g., spectroscopy, the amount of the compound released over time. For example, and without limitation, the filament or filaments release no more than from 1 ng to 100 μg of the genipin or crosslinking genipin derivative into the aneurysm sac per day. For example, in use, and/or when placed in an aqueous solvent, such as water, PBS, saline, or plasma, a 10 cm length of a filament as described in any embodiment presented herein releases between 1 ng and 100 μg of genipin per day. It should be noted that the genipin-releasing or crosslinking genipin derivative-releasing filaments described herein can be deployed in fixed lengths into an aneurysm fundus, and additional filaments that do not release the compound can be used to fill the aneurysm. This method may be used to control the amount of the compound released into the fundus.

Example

Safety and efficacy of the vaso-occlusive devices are tested as follows. Embolism coils are prepared by coating platinum, platinum alloy or nitinol embolism coil, optionally pre-coated with a hydrogel, with a layer of PLGA (25%, 50% and 75% lactic acid, molar feed ratio). The PLGA is mixed with 0.0, 0.01, 0.1, 0.25, 0.5, 1.0, 5.0 and 10.0 mg/mL genipin or a crosslinking genipin derivative. The coils are dried, sterilized and stored at room temperature. One or more of the coils, and control coils (no hydrogel and/or 0.0 mg/mL of active compound), are tested in a rabbit model, essentially as shown in Reinges, M. H. T, et al., *Interventional Neuroradiology* (2010) 16:139-150.

The present invention has been described in accordance with several examples, which are intended to be illustrative in all aspects rather than restrictive. Thus, the present invention is capable of many variations in detailed implementation, which may be derived from the description contained herein by a person of ordinary skill in the art.

We claim:

1. A method of creating and stabilizing a blood clot in a patient, comprising:
   inducing clot formation in a patient's vasculature; and
   contacting the clot with genipin or a crosslinking genipin derivative to stabilize the clot.

2. The method of claim 1, wherein the genipin or a crosslinking genipin derivative is incorporated into a bioerodible polymer.

3. The method of claim 1, wherein the step of inducing clot formation in the patient comprises feeding a vaso-occlusive device into the patient's vasculature to induce clot formation.

4. The method of claim 3, wherein the vaso-occlusive device is an embolism coil.

5. The method of claim 3, wherein the genipin or crosslinking genipin derivative comprises a filament comprising core and a controlled release coating layer on the core comprising the genipin or a crosslinking genipin derivative.

6. The method of claim 5, wherein the filament comprises between the core substrate and the controlled release coating layer a polymeric intermediary layer.

7. The method of claim 6, wherein the polymeric intermediary layer is a hydrogel, or wherein the controlled release coating layer is a non-bioerodible polymer comprising the genipin or crosslinking genipin derivative.

8. The method of claim 3, wherein the genipin or crosslinking genipin derivative is provided as a filament comprising a controlled-release genipin or crosslinking genipin derivative.

9. The method of claim 1, wherein the clot is contacted with a crosslinking derivative of genipin.

10. The method of claim 9, wherein the cross-linking derivative of genipin is a compound according to formula 2, or a stereoisomer or pharmaceutically acceptable salt thereof:

2 where R1 is —H, =O or —OR4, where R4 is —H, $C_{1-6}$ alkyl, $C_{1-3}$ alkyl, or $C_{1-12}$ alkanoyl which can be substituted with phenyl, phenoxy, pyridyl or thienyl;
R2 is H, $C_{1-6}$ alkyl, $C_{1-3}$ alkyl, methyl, ethyl, propyl, isopropyl, butyl, n-butyl, t-butyl, isobutyl, or sec-butyl; and
R3 is a primary alcohol chosen from —CH$_2$—OH and —R5-CH$_2$—OH, where —R5- is $C_{1-6}$ alkyl, $C_{1-3}$ alkyl, methyl, ethyl, propyl, isopropyl, butyl, n-butyl, t-butyl, isobutyl, or sec-butyl, other than genipin.

11. The method of claim 10, wherein R1 is —OR4, where R4 is —H or $C_{1-3}$ alkyl.

12. The method of claim 11, wherein R2 is H or $C_{1-3}$ alkyl and/or R3 is —CH$_2$—OH, —CH$_2$—CH$_2$—OH, or —CH$_2$—CH$_2$—CH$_2$—OH.

13. The method of claim 10, wherein R2 is H or $C_{1-3}$ alkyl.

14. The method of claim 10, wherein R3 is —CH$_2$—OH, —CH$_2$—CH$_2$—OH, or —CH$_2$—CH$_2$—CH$_2$—OH.

15. A vaso-occluding catheter device comprising a sheath and first and second filaments within the sheath, wherein the second filament comprises, as a core substrate or a coating thereon, genipin or a crosslinking genipin derivative.

16. The device of claim 15, wherein the crosslinking derivative of genipin is a compound according to formula 2, or a stereoisomer or a pharmaceutically acceptable salt thereof:

2 where R1 is —H, =O or —OR4, where R4 is —H, $C_{1-6}$ alkyl, $C_{1-3}$ alkyl, or $C_{1-12}$ alkanoyl which can be substituted with phenyl, phenoxy, pyridyl or thienyl;
R2 is H, $C_{1-6}$ alkyl, $C_{1-3}$ alkyl, methyl, ethyl, propyl, isopropyl, butyl, n-butyl, t-butyl, isobutyl, or sec-butyl; and
R3 is a primary alcohol chosen from —CH$_2$—OH and —R5-CH$_2$—OH, where —R5- is $C_{1-6}$ alkyl, $C_{1-3}$ alkyl, methyl, ethyl, propyl, isopropyl, butyl, n-butyl, t-butyl, isobutyl, or sec-butyl, other than genipin.

17. The device of claim 16, wherein R1 is —OR4, where R4 is —H or $C_{1-3}$ alkyl.

18. The device of claim 17, wherein R2 is H or $C_{1-3}$ alkyl and/or R3 is —CH$_2$—OH, —CH$_2$—CH$_2$—OH, or —CH$_2$—CH$_2$—CH$_2$—OH.

19. The device of claim 16, wherein R2 is H or $C_{1-3}$ alkyl.

20. The device of claim 16, wherein R3 is —CH$_2$—OH, —CH$_2$—CH$_2$—OH, or —CH$_2$—CH$_2$—CH$_2$—OH.

* * * * *